(12) United States Patent
Bajgrowicz et al.

(10) Patent No.: US 6,441,052 B1
(45) Date of Patent: Aug. 27, 2002

(54) CYCLOPENTYLALKYL-NITRILES

(75) Inventors: Jerzy A. Bajgrowicz, Zürich; Bernadette Bourdin Trunz, Genève; Peter Gygax, Fällanden, all of (CH)

(73) Assignee: Givaudan SA (CH)

( * ) Notice: Subject to any disclaimer, the term of this patent is extended or adjusted under 35 U.S.C. 154(b) by 0 days.

(21) Appl. No.: 10/121,519

(22) Filed: Apr. 12, 2002

Related U.S. Application Data

(62) Division of application No. 09/609,845, filed on Jul. 5, 2000.

(30) Foreign Application Priority Data

Jul. 5, 1999 (EP) .............................. 99810585

(51) Int. Cl.$^7$ ..................... A61K 31/12; A61K 31/11; C07C 49/105; C07C 35/06

(52) U.S. Cl. ................ 514/690; 514/693; 514/729; 565/379; 565/420; 565/838

(58) Field of Search ................ 514/690, 693, 514/729; 568/379, 420, 838

(56) References Cited

U.S. PATENT DOCUMENTS 5,696,075 A * 12/1997 Chapuis et al. ............... 512/6
6,084,138 A *  7/2000 Aida et al. .................... 568/838

* cited by examiner

*Primary Examiner*—T. A. Solola
*Assistant Examiner*—Joseph Murray
(74) *Attorney, Agent, or Firm*—Fish & Richardson P.C.

(57) ABSTRACT

The present invention provides compounds of formula I

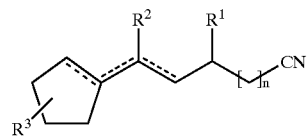

wherein
$R^1$ and $R^3$ are independently H or $C_{1-3}$ alkyl, and $R^2$ is H, $C_{1-3}$ alkyl, methylene or ethylidene, with the proviso that $R^1$ and $R^2$ are not simultaneously H;
n is 0 or 1; and
=== is a single or a double bond, wherein a maximum of two double bonds are present in the compound. Compounds of formula II are also provided:

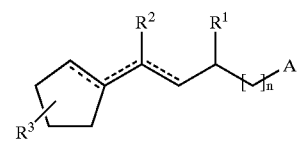

wherein
A is selected from the group of $CR^4R^5OH$, $CR^4R^5OC(O)R^6$, $CO_2R^6$, CN and $C(O)R^4$;
$R^1$, $R^3$, $R^4$, and $R^5$ are independently H or $C_{1-3}$-allyl;
$R^2$ is H, $C_{1-3}$-alkyl, methylene, or ethylidene;
$R^6$ is H, $C_{1-3}$ alkyl, $C_{2-4}$ alkenyl, or alkinyl;
n is 0 or 1; and
=== is a single or a double bond, wherein a maximum of two double bonds are present. Compositions containing compounds of formulae I and II, as well as methods for imparting fragrance to substrates using such compounds are also provided.

3 Claims, No Drawings

CYCLOPENTYLALKYL-NITRILES

The instant application is a divisional application of 09/609,845 filed on Jul. 5, 2000.

FIELD OF THE INVENTION

The present invention provides new cyclopentylalkyl-nitriles and methods for applying to a substrate a fragrance made from such compounds.

BACKGROUND OF THE INVENTION

Despite the common occurrence of five-membered carbon rings in perfumery ingredients, mainly of terpenic origin (e.g. campholenic aldehyde derivatives of sandalwood-type odor note) or resulting from a Diels-Alder condensation with inexpensive cyclopentadiene, very few of such structures contain an unsubstituted, isolated (i.e. not part of a polycyclic fused or spiro system) cyclopentyl, cyclopentenyl or cyclopentylidene radical. The following products are among the few examples of such perfumery raw materials:

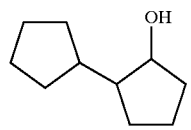
CAS 4884-25-7

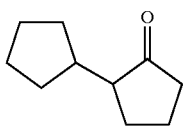
CAS 4884-24-6

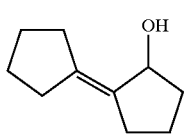
CAS 6261-30-9

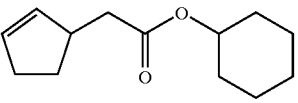
CAS 68039-73-6

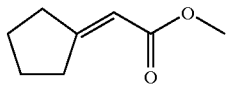
CAS 40203-73-4

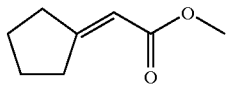
CAS 65405-69-8

These compounds are also disclosed in EP 0 016 650, EP 0 770 671 and U.S. Pat. Nos. 4,280,934 and 4,338.458.

SUMMARY OF THE INVENTION

There is a renewed interest in floral fragrances. Therefore, an object of the present invention is to provide new perfumery ingredients exhibiting original, intense, diffusive and substantive (i.e. long-lasting) scents belonging to the floral family.

One embodiment of the invention is a compound of formula I:

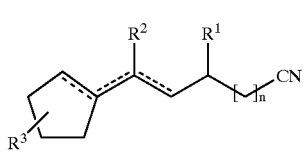

wherein
$R^1$ and $R^3$ are independently H or $C_{1-3}$ alkyl, and $R^2$ is H, $C_{1-3}$ alkyl, methylene or ethylidene, with the proviso that $R^1$ and $R^2$ are not simultaneously H;

n is 0 or 1; and
=== is a single or a double bond, wherein a maximum of two double bonds are present in the compound. These compounds possess very intense, mainly rosy and orris notes.

Another embodiment of the invention is a compound of formula II:

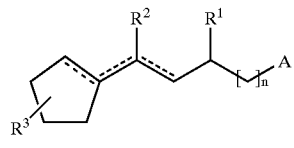

wherein
A is selected from the group of $CR^4R^5OH$, $CR^4R^5OC(O)R^6$, $CO_2R^6$, $CN$ and $C(O)R^4$;
$R^1$, $R^3$, $R^4$, and $R^5$ are independently H or $C_{1-3}$-alkyl;
$R^2$ is H, $C_{1-3}$-alkyl, methylene, or ethylidene;
$R^6$ is H, $C_{1-3}$ alkyl, $C_{2-4}$ alkenyl, or alkinyl;
n is 0 or 1; and
=== is a single or a double bond, wherein a maximum of two double bonds are present. These compounds possess interesting olfactory properties. The odors are mainly floral, e.g. lily of the valley, orris or ylang-ylang and fruity, e.g. citrus. They are intense, diffusive and long lasting. All compounds of the general formula II have substantive odors, a quality crucial for functional perfumery.

DETAILED DESCRIPTION OF THE INVENTION

As noted above, the invention provides a compound of formula I:

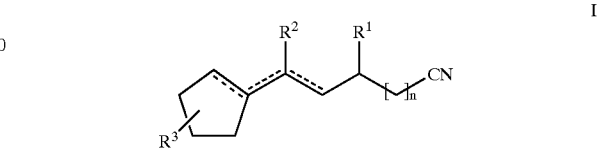

wherein
$R^1$ and $R^3$ are independently H, or $C_{1-3}$ alkyl, and $R^2$ is H, $C_{1-3}$ alkyl, methylene or ethylidene; with the proviso that $R^1$ and $R^2$ are not simultaneously H;
n is 0 or 1; and
=== is a single or a double bond, wherein a maximum of two double bonds are present in the compound.

The invention also provides a method of using the compounds of formula II

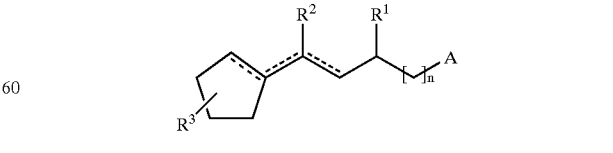

wherein
A is selected from the group of $CR^4R^5OH$, $CR^4R^5OC(O)R^6$, $CO_2R^6$, $CN$ or $C(O)R^4$;
$R^1$, $R^3$, $R^4$, and $R^5$ are independently H or $C_{1-3}$-alkyl;

$R^2$ is H, $C_{1-3}$-alkyl, methylene or ethylidene;

$R^6$ is H, $C_{1-3}$-alkyl, $C_{2-4}$ alkenyl, or alkinyl;

n is 0 or 1; and

══ is a single or a double bond, wherein a maximum of two double bonds are present.

The heteroatoms in all compounds of formula I and II of the present invention are in a more remote position relative to the lipophilic cyclopentane ring than the oxygen atoms in the corresponding known perfumery ingredients.

The compounds of formula II may be used to impart odor to any perfumery composition, such as for example fine and functional perfumery, e.g. perfumes, fine fragrance accords or detergents, fabric softeners, shower gels, soaps, cosmetics, scented candles, and the like.

The compounds of formula I are new. The following is an exemplary list of compounds of formula II which are also new:

5-Cyclopentyl-3-methylpent-4-en-1-ol
5-Cyclopentyl-3-methylpent-4-enal
5-Cyclopentyl-3-methylpent-4-en-1-yl acetate
5-Cyclopentyl-3-methylpentan-1-ol
4-Cyclopentylpentan-1-ol
4-Cyclopentylpent-1-yl propanoate
4-Cyclopentylpentanal
Ethyl-4-cyclopentylpentanoate
5-Cyclopentylhexan-2-one
5-Cyclopentylhexanal
5-Cyclopentylhexan-1-ol
5-(2-Methylcyclopent-1-enyl)pentan-1-ol
5-(5-Methylcyclopent-1-enyl)pentan-1-ol
4-Cyclopentylidenebutan-1-ol
6-Cyclopentyl-3-methylhexan-3-ol
5-(Cyclopent-1-enyl)-2-methylpentan-2-ol
5-Cyclopentylpentan-2-ol
5-Cyclopentylidene-2-methylpentan-2-ol
5-Cyclopentylidenepent-2-yl propanoate The following compounds of formula I are preferred:

5-Cyclopentyl-3-methylpentanenitrile
4-Cyclopentylpentanenitrile
5-Cyclopentylhexanenitrile
5-Cyclopentylidenehexanenitrile
5-(Cyclopent-1-enyl)hexanenitrile The compounds of formulae I and II may be prepared by different synthetic ways. For example, the five-membered ring may be introduced with commercially available starting materials (cyclopentanone, cyclopentadiene, cyclopentylhalogenide and derivatives) or, prepared by 1,4-dihalogenobutane-derived Grignard reagent addition to lactones. Among the best methods for synthesizing functionalized cyclopentyl-, cyclopentenyl- or cyclopentylidene-alkanes are the cyclopentadienyl anion addition to carbonyl groups, followed by a total or partial hydrogenation of the thus formed fulvene structure, as depicted in scheme I (See, e.g. Coe, J.; Vetelino, M. G.; Kemp, D. S. *Tetrahedron Lett.* 1994, 35, 6627).

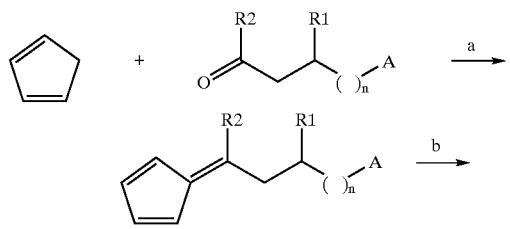

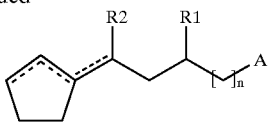

wherein "a" is piperidine and "b" is hydrogenation.

The odorant compounds of formula II may be combined with numerous odorant ingredients of natural and/or synthetic origin, wherein the range of the natural odorants may include not only readily volatile, but also moderately and only slightly volatile components. The synthetic odorants may embrace representatives from practically all classes of substances. The following non-limiting list includes examples of known odorant compositions which may be combined with the compounds of the invention:

natural products such as tree moss absolute, basil oil, tropical fruit oils (such as bergamot oil, mandarin oil, etc.), mastix absolute, myrtle oil, palmarosa oil, galbanum oil, patchouli oil, petitgrain oil, wormwood oil, lavender oil, rose oil, jasmine oiL ylang-ylang oil, and the like;

alcohols such as farnesol, geraniol, linalool, nerol, phenylethyl alcohol, rhodinol, cinnamic alcohol, (Z)-hex-3-en-1-ol, menthol, α-terpineol, and the like;

aldehydes such as citral, α-hexyl cinnamaldehyde, LIL-IALS® (Givaudan Roure), hydroxycitronellal, methylnonylacet-aldehyde, phenylacetaldehyde, anisaldehyde, vanillin, and the like;

ketones such as allylionones, α-ionone, β-ionone, ISOR-ALDEINE® (Givaudan Roure), methylionone, verbenone, nootkatone, geranylacetone, and the like;

esters such as allyl phenoxyacetate, benzyl salicylate, cinnamyl propionate, citronellyl acetate, decyl acetate, dimethylbenzylcarbinyl acetate, dimethylbenzylcarbinyl butyrate, ethyl acetoacetate, cis-3-hexenyl isobutyrate, cis-3-hexenyl salicylate, linalyl acetate, methyl dihydrojasmonate, styralyl propionate, vetiveryl acetate, benzyl acetate, geranyl acetate, and the like;

lactones such as γ-undecalactone, δ-decalactone, pentadecanolide, 12-oxahexadecanolide, and the like;

acetals such as Viridine (phenylacetaldehyde dimethylacetal), and the like; and various components often used in perfumery such as indole, p-mentha-8-thiol-3-one, methyleugenol, eugenol, aneihol, and the like.

The novel odorants harmonize particularly well with all other floral notes (lily of the valley, rose, orris, jasmine, ylang-ylang, narcissus notes, and the like), as well as with woody, chypre and animalic notes, tobacco-like and patchouli compositions, and the like.

The amount of a compound according to the present invention that may be combined with such odorant compositions may vary within wide limits ranging from a few parts per thousand in mass market products (e.g. cleaning or deodorant products) up to a few percent in alcoholic extracts for (fine) perfumery. In all cases, even in small amounts, the compounds of the present invention provide odorant compositions with intense floral notes with increased volume (strength, diffusivity) and substantivity of the odor. In particular, the manner in which the present compounds extend the diffusivity and the olfactory duration of such odorant compositions is remarkable.

There is no restriction regarding the type of fragrance formulations that may be combined with the compounds of the present invention. Nor is there a limitation on the destination of the actual finished product. Non-limiting examples of suitable formulations/finished products include eau de cologne, toilet water, scented water, perfume, cream, shampoo, deodorant, soap, detergent powder, household cleaner, fabric softener, and the like.

In the following examples, all compounds were identified by their $^1$H-NMR-, IR- and MS-spectra under the following conditions:

IR: Nicolet 510 FT-IR, neat, ν in cm$^{-1}$;

$^1$H NMR: Bruker DPX-400 at 250 and 400 MHz; in CDCl$_3$, if not otherwise stated; chemical shifts (d) in ppm downfield from TMS, coupling constants J in Hz; and MS and GC/MS: Finnigan MAT 212 (EI, 70eV), intensities (in brackets) in % rel. to the base peak.

They were always purified by fractional distillation, or bulb-to-bulb distillation, if after flash chromatography (Merck silica gel 60; 230–400 mesh), and were olfactorily pure, colorless oils.

The following examples are provided to further illustrate the compounds of the present invention. These examples are illustrative only and are not intended to limit the scope of the invention in any way.

EXAMPLES

Example 1

5-Cyclopentyl-3-methylpent-4-en-1-ol

A solution of ethyl 5-cyclopentyl-3-methylpent-4-enoate (16.8 g; 80 mmol; obtained according to Streinz, L., Romanuk, M., Sorm, F., Sehnal, F. DE 2 444 837, priority Sep. 20, 1973) in diethyl ether (30 ml) was added dropwise to a suspension of lithium aluminum hydride (3.0 g; 80 mmol) in the same solvent (110 ml), and the reaction mixture was stirred at reflux for 1 hour. Water (3.5 ml), then 15% NaOH solution, and again water (3.5 ml) were added, the precipitate filtered off and washed with MTBE (30 ml). The combined organic phases were washed with 1 NHCl (200 ml) and brine (3×100 ml), dried (MgSO$_4$), concentrated in vacuo, and distilled (79–82° C./0.07 torr) to give 7.8 g (59% yield) of 5-cyclopentyl-3-methylpent-4-en-1-ol.

IR: 3329, 2953, 2869, 1453, 1373, 1052, 999, 969. $^1$H-NMR: 0.98 (d, J=6.7, 3H), 1.16–1.40 (m, 2H), 1.46–1.82 (m, 9H), 2.12–2.28 (m, 1H), 2.26–2.47 (m, 1H), 3.64 (t, J=6.6 Hz), 5.25 (dd, J=15.3, 7.3, 1H), 5.41 (dd, J=15.3, 7.0, 1H). MS: 168 (1.3, M$^+$), 150 (3), 135 (8), 121 (9), 108 (8), 107 (9), 95 (64), 93 (31), 82 (63), 81 (93), 79 (40), 69 (35), 67 (100), 55 (59),41 (57).

Odor: floral, fruity, hesperidic/citrus, very strong and substantive.

Example 2

5-Cyclopentyl-3-methylpent4-enal

Diisobutylaluminum hydride (95 ml of 1.0 M solution in hexane) was added into a hexane (200 ml) solution of ethyl 5-cyclopentyl-3-methylpent-4-enoate (used in example 1; 20.0 g; 95 mmol), at −65° C. After 3 hours stirring at the same temperature, ethanol (3 ml) was added, and the reaction mixture was poured into an ice-cold NH$_4$Cl solution (200 ml) and diluted with 2 NHCl (100 ml). The organic layer was separated, washed with brine (3×200 ml), dried (MgSO$_4$), concentrated in vacuo, and purified by flash chromatography (hexane/MTBE 15:1) to give 10.9 g (69% yield) of 5-cyclopentyl-3-methylpent-4-enal.

IR: 2954, 2870, 2716, 1727, 1453, 1375, 970. $^1$H-NMR: 1.06 (d, J=7.0, 3H), 1.12–1.36 (m, 2H), 1.44–1.83 (m, 6H), 2.25–2.49 (m, 3H), 2.61–2.81 (m, J=6.7, 1H), 5.32 (dd, J=15.4, 6.1, 1H), 5.44 (dd, J=15.4, 6.4, 1H), 9.71 (t, J=2.3, 1H). MS: 166 (1.5, M$^+$), 151 (3), 148 (3), 122 (61), 107 (15), 98 (43), 97 (57), 95 (44), 93 (64), 81 (63), 80 (36), 79 (47), 69 (47), 67 (100), 55 (71), 41 (88), 39 (41).

Odor: aldehydic, citrus, geranium.

Example 3

5-Cyclopentyl-3-methylpent-4-en-1-yl acetate

Acetyl chloride (1.7 g; 22 mmol) was added to a cooled solution of 5-cyclopentyl-3-methylpent-4-en-1-ol (obtained in example 1; 2.6 g; 15 mmol), pyridine (2.4 g; 30 mmol), and DMAP (0.13 g; 0.1 mmol) in cyclohexane (65 ml). After 3 hours stirring at room temperature, the reaction mixture was poured into 1NHCl (130 ml) and MTBE (65 ml). The organic layer was separated, washed successively with 1NHCl (130 ml), sodium bicarbonate solution (100 ml) and brine (2×100 ml) and treated as in example 1 (distillation at 120° C./0.8 torr) to give 3.05 g (94% yield) of 5-cyclopentyl-3-methylpent-4-en-1-yl acetatate.

IR: 2954, 2869, 1743, 1454, 1366, 1238, 1048, 970. $^1$H-NMR: 0.99 (d, J=6.7, 3H), 1.13–1.34 (m, 2H), 1.44–1.83 (m, 8H), 2.04 (s, 3H), 2.08–2.30 (m, J=7.0, 1H), 2.26–2.47 (m, 1H), 4.05 (t, J=6.8, 2H), 5.20 (dd, J=15.4, 7.3, 1H), 5.37 (dd, J=15.4, 7.0, 1H). MS: 195 (0.1, M$^+$—CH$_3$), 150 (10), 135 (13), 121 (18), 108 (13), 107 (11), 95 (18), 93 (29), 82 (22), 81 (100), 80 (23), 79 (25), 67 (43), 55 (28), 41 (27).

Odor: fruity, pear, pineapple, floral.

Example 4

5-Cyclopentyl-3-methylpentan-1-ol

Ethyl 5-cyclopentyl-3-methylpent4-enoate of example 1 (22.4 g; 0.11 mol) was hydrogenated over 5% Pd/C in ethanol (220 ml), at room temperature and under atmospheric pressure. The catalyst was filtered off, the solvent evaporated in vacuo and the residue distilled (59° C./0.08 torr) to give 19.5 g (92% yield) of 5-cyclopentyl-3-methylpentanoate that was reduced with lithium aluminum hydride as in example 1 to give 5-cyclopentyl-3-methylpentan-1-ol in 76.5% yield.

IR: 3331, 2949, 2867, 1454, 1377, 1059, 1010. $^1$H-NMR: 0.89 (d, J=6.4, 3H), 0.97–1.84 (m, 17H), 3.68 (m, 2H). MS: 152 (0.4, M$^+$—H$_2$O), 137 (11), 124 (21), 123 (16), 110 (12), 109 (14), 95 (85), 82 (100), 71 (28), 69 (72), 67 (77), 55 (77), 41 (51).

Odor: very strong, rosy, geranium, woody.

Example 5

5-Cyclopentyl-3-methylpentanenitrile a) 5-Cyclopentyl-3-methylpentanal oxime

An aqueous (7 ml) solution of hydroxylamine hydrochloride (3.9 g; 56 mmol) was added to an ethanolic (20 ml) solution of 5-cyclopentyl-3-methylpentanal (8.0 g; 47 mmol), obtained from ethyl 5-cyclopentyl-3-methylpentanoate of example 4 by diisobutylaluminum hydride reduction according to example 2 (73% yield). The reaction mixture was heated to 50° C. and treated with a solution of sodium hydroxide (2.7 g; 67 mmol) in water (5 ml). After 2 hours stirring at room temperature, ice (25 g) was added, and the mixture was saturated with carbon dioxide (solid). The organic layer was separated, dried (MgSO$_4$), concentrated in vacuo, and purified by flash chromatography (MTBE/hexane 1:4) to give 5.8 g (67% yield) of 5-cyclopentyl-3-methylpentanal oxime.

b) 5-Cyclopentyl-3-methylpentanenitrile 5-cyclopentyl-3-methylpentanal oxime (3.7 g; 20 mmol) and acetic anhydride (4.5 g; 40 mmol) were heated at 110° C. during 1.5 hours, poured into ice-water (100 ml), and extracted with MTBE (150 ml). The organic phase was washed with brine (4×150 ml), dried (MgSO$_4$), concentrated in, vacuo, and purified by flash chromatography (MTBE/hexane 1:15) to give 1.9 g (57% yield) of 5-cyclopentyl-3-methylpentanenitrile.

IR: 2950, 2866, 2246, 1457, 1425, 1384. $^1$H-NMR: 1.06 (d, J =6.7, 3H), 1.25–1.91 (m, 14H), 2.22 (dd, J=16.7, 6.3, 1H), 2.33 (dd, J=16.7, 6.0, 1H). MS: 165 (0.5, M$^+$), 164 (5), 150 (12), 136 (23), 124 (100), 122 (26), 109 (14), 97 (27), 94 (19), 83 (14), 82 (15), 69 (48), 68 (45), 55 (66), 41 (88).

Odor: citrus, geranitrile, peach, rosy.

Example 6

4-Cyclopentylpentan-1-ol a) 4-Cyclopentyl entanoic acid

4-Cyclopenta-2,4-dienylidenepentanoic acid (25 g; 0.15 mol; obtained according to Coe, J. W.; Vetelino, M. G.; Kemp, D. S., *Tetrahedron Lett.*, 1994, 35, 6627.) in ethyl acetate (270 ml) was hydrogenated as in example 4 to give 23.6 g (92% yield) of crude 4-cyclopentylpentanoic acid which was used in the next step without further purification.

b) 4-Cyclopentylpentan-1-ol

A solution of 4-cyclopentylpentanoic acid (16 g; 94 mmol) in diethyl ether (30 ml) and THF (30 ml) was added within 20 minutes to lithium aluminum hydride (3.6 g; 94 mmol) and suspended in the same solvent (100 ml). After 2 hours at reflux, the reaction mixture was cooled with an ice-bath and quenched successively with water (4 ml), 15% sodium hydroxide (12 ml) and again water (4 ml). The white solid was filtered off, and the mixture diluted with MTBE (300 ml), washed with 1 N HCl (300 ml), sodium bicarbonate solution (300 ml) and brine (2×300 ml), dried (MgSO$_4$), concentrated in vacuo, and distilled (59° C./0.075 torr) to give 8.7 g (59% yield) of 4-cyclopentylpentan-1-ol.

IR: 3329, 12950, 2867, 1451, 1377, 1056, 894. $^1$H-NMR: 0.88 (d, J=6.4, 3H), 1.0–1.81 (m, 15H), 3.62 (m, 2H);. MS: 138 (3, M$^+$—H$_2$O), 123 (3), 110 (42), 109 (14), 97 (58), 96 (40), 95 (35), 87 (24), 81 (27), 68 (38), 67 (51), 55 (60), 41 (43).

Odor: floral, woody, citrus, metallic.

Example 7

4-Cyclopentylpent-1-yl propanoate

4-Cyclopentylpentan-1-ol (4.0 g; 23 mmol) was esterified with propionyl chloride (3.1 g; 34 mmol) according to example 3 to give 4.4 g (84.5% yield) of 4-cyclopentylpent-1-yl propanoate.

IR: 2951, 2868, 1743, 1456, 1366, 1239, 1048. $^1$H-NMR: 0.87 (d, J=6.4, 3H), 1.00–1.87 (m, 14H), 1.14 (t, J=7.5, 3H), 2.32 (q, J=7.6, 2H), 4.05 (t, J=6.6, 2H). MS: 226 (0.01, M$^+$), 197 (4), 152 (10), 137 (12), 124 (17), 123 (18), 110 (22), 96 (32), 95 (88), 83 (50), 82 (100), 81 (42), 75 (40), 69 (44), 67 (59), 57 (67), 55 (53), 41 (32).

Odor: orange, fruity, ozonic, floral.

Example 8

Ethyl 4-cyclopentylpentanoate 1,1'-Carbonyldiimidazole (101 g; 0.62 mmol) was added portionwise to 4-cyclopentylpentanoic acid (100 g; 0.58 mol) in THF (500 ml). After the gas evolution ceased, the reaction mixture was reacted with sodium ethylate solution prepared from sodium (0.3 g; 13 mmol) and ethanol (500 ml), stirred at room temperature for 2.5 hours, and the solvent evaporated in vacuo. The residue was dissolved in ether (300 ml), washed successively with water (300 ml), 1 N NaOH (300 ml), and 1 N HCl (300 ml), dried (MgSO$_4$), concentrated in vacuo, and distilled over a 10 cm Vigreux column (66° C./0.08 torr) to give 59.4 g (52% yield) of ethyl 4-cyclopentylpentanoate.

IR: 2953, 2869, 1738, 1451, 1376, 1253, 1181, 1104, 1037, 939. $^1$H-NMR: 0.87 (d, J=6.4, 3H), 1.26 (t, J=7.2, 3H), 1.01–1.91 (m, 12H), 2.23 (ddd, J=15.3, 8.8, 6.4, 1H), 2.37 (ddd, J=15.3, 9.8, 5.5, 1H), 4.12 (q, J=7.1, 2H). MS: 183 (0.1, M$^{+-CH_3}$), 153 (3), 141 (16), 135 (32), 129 (23), 111 (65), 110 (31), 101 (98), 88 (85), 69 (49), 67 (36), 55 (100), 41 (67).

Odor: green, fruity (pineapple), floral (rosy).

Example 9

4-Cyclopentylpentanal

Ethyl 4-cyclopentylpentanoate was reduced to 4-cyclopentylpentanal with diisobutylaluminum hydride as in example 2 (68% yield).

IR: 2952, 2868, 2714, 1727, 1450, 1411, 1379, 1012. $^1$H-NMR: 0.88 (d, J=6.4, 3H), 1.01–1.91 (m, 12H), 2.29–2.57 (m, 2H), 9.77 (t, J=2.0, 1H). MS: 154 (4, M$^+$), 139 (10), 136 (18), 121 (19), 110 (77), 97 (44), 95 (53), 85 (36), 81 (35), 69 (62), 68 (76), 67 (100), 55 (76), 41 (60).

Odor: aldehydic, melon, mandarin, green ivy, floral.

Example 10

4-Cyclopentylpentanenitrile

4-Cyclopentylpentanal was transformed into 4-cyclopentyl-pentanenitrile as in example 5 (56% yield).

IR: 2953, 2869, 2246, 1450, 1428, 1381. $^1$H-NMR: 0.91 (d, J=6.1, 3H), 1.04–1.26 (m, 2H), 1.36–1.93 (m, 10H), 2.21–2.49 (m, 2H). MS: 151 (0.1, M$^+$), 150 (0.5), 136 (4), 123 (3), 110 (45), 109 (43), 97 (11), 83 (18), 69 (63), 68 (19), 67 (21), 55 (83), 41 (100).

Odor: hesperidic, floral, green, cumin.

Example 11

5-Cyclopentylhexanenitrile a) 5-(Cyclopenta-2,4-dienylidene)hexanenitrile

Pyrrolidine (18.5 g; 0.26 mol) was added to a solution of cyclopentadiene (10.8 g; 0.16 mol; freshly prepared by cracking of dicyclopentadiene) and 5-oxohexanenitrile (15.4 g; 0.13 mol) in methanol (175 ml) at 0° C. After 1 hour stirring at this temperature, the reaction mixture was poured into ice-cold 2 NHCl (500 ml), saturated with sodium chloride, and extracted with MTBE (400 ml). The organic phase was washed with brine (3×300 ml), dried (MgSO$_4$), concentrated in vacuo, and used in the next step without further purification.

b) 5-Cyclopentylhexanenitrile

Hydrogenation as in example 4 gave 5-cyclopentyl-hexanenitrile.

IR: 2952, 2868, 2245, 1458, 1427, 1378. $^1$H-NMR: 0.88 (d, J=6.1, 3H), 1.01–1.86 (m, 14H), 2.28–2.37 (m, 2H). MS: 165 (2, M$^+$), 164 (12), 150 (25), 136 (17), 124 (67), 122 (39), 98 (61), 97 (100), 96 (47), 82 (34), 69 (80), 68 (38), 67 (25), 55 (71), 41 (49).

Odor: floral, orris, spicy, powdery, cumin.

Example 12

5-Cyclopentylhexan-2-one

4-Cyclopentylpentanoic acid (3.4 g; 20 mmol; prepared in example 6) in diethyl ether (90 ml) was added at 0° C. to 1.6 M diethyl ether solution of methyllithium (25 ml; 40 mmol), and diluted with the same solvent (75 ml). After 3.5 hours stirring at 5° C., water (100 ml) was added, and the separated organic layer was washed with brine (3×400 ml), dried ($MgSO_4$), concentrated in vacuo, and bulb-to-bulb distilled (125° C./0.2 torr) to give 1.8 g (53.5% yield) of 5-cyclopentylhexan-2-one.

IR: 2952, 2868, 1718, 1450, 1412, 1357, 1162. $^1$H-NMR: 0.86 (d,J=6.1, 3H), 1.02–1.85 (m, 12H), 2.15 (s, 3H), 2.28–2.57 (m, 2H). MS: 168 (5, M$^+$), 150 (12), 135 (21), 121 (96), 111 (79), 110 (70), 108 (46), 81 (27), 71 (46), 69 (58), 67 (58), 58 (55), 55 (57), 43 (100), 41 (35).

Odor: fruity, lavender, orris, lactonic, pineapple.

Example 13

5-Cyclopentylidenehexanenitrile and 5-(cyclopent-1-enyl)-hexanenitrile a) 5-Cyclopentyl-5-hydroxyhexanenitrile 5-Oxohexanenitrile (11.1 g; 0.10 mmol) was added at 20° C. to a suspension of anhydrous cerium(III) chloride (30 g; 0.12 mol) in THF (250 ml). After 1 hour stirring at room temperature, cyclopentylmagnesium chloride (60 ml of 2.0 M solution in diethyl ether; 0.12 mol) was added dropwise at 5° C. and stirring continued for more 0.5 hour at the same temperature. 2 N HCl (60 ml) was added, and the reaction mixture was extracted with MTBE (2×200 ml). The combined organic phases were washed with 2 N HCl (100 ml), and brine (2×100 ml), dried ($MgSO_4$), and concentrated in vacuo, to give 13 g of crude (83% GC pure; 60% yield) 5-cyclopentyl-5-hydroxyhexanenitrile. The 5-cyclopentyl-5-hydroxyhexanenitrile was used without further purification in the next step.

b) 5-Cyclopentylidenehexanenitrile and 5-(cyclopent-1-enyl)hexanenitrile

Crude 5-cyclopentyl-5-hydroxyhexanenitrile (18 g; 0.1 mol) from example 13(a) was added into a solution of sulphuric acid (15 ml) in acetic acid (150 ml). The reaction mixture was stirred at 5° C. for 1 hour, then poured into ice (100 g), diluted with MTBE (100 ml), washed with saturated sodium bicarbonate solution (5×300 ml) and brine (2×300 ml), dried ($MgSO_4$), concentrated in vacuo, and bulb-to-bulb distilled to give 2.1 g (13% yield) of 5-cyclopentylidene-hexanenitrile and 5-(cyclopent-1-enyl)-hexanenitrile mixture (GC: 43+57%).

IR: 2953, 2867, 2245, 1457, 1433, 1377. $^1$H-NMR: 1.03 (d, J=6.7, 1.5H), 1.41–1.66 (m, 4H), 1.60 (s, 1.5H), 1.75 (m, J=7.3, 1H), 1.84 (m, J=7.4, 1H), 2.11–2.38 (m, 7.5H), 5.36 (m, 0.5H). MS (major product): 163 (26, M$^+$), 148 (62), 135 (20), 134 (23), 120 (32), 107 (66), 95 (77), 91 (24), 79 (32), 77 (25), 67 (100), 55 (29), 41 (42); MS (minor product): 163 (13, M$^+$), 163 (6), 148 (28), 135 (18), 134 (12), 120 (38), 107 (31), 95 (100), 91 (18), 79 (24), 77 (20), 67 (93), 55 (20), 41 (33).

Odor: cumin, orris, spicy, floral, stronger than 5-cyclopentylhexanenitrile.

Example 14

5-Cyclopentylhexanal

Diisobutylaluminum hydride (60 ml of 1.0 M solution in hexane) was added at −65° C. to a hexane (50 ml) solution of 5-cyclopentylhexanenitrile (5.0 g; 30 mmol; from example 11). After stirring at −70° C. for 0.5 hour, and at room temperature for 3 hours, methanol (1.8 ml) was added, and the stirring continued for 20 minutes. 10% $H_2SO_4$ (48 ml) was added, and the reaction mixture was diluted with MTBE (150 ml). The organic layer was separated, washed with saturated sodium bicarbonate solution (300 ml) and brine (3×300 ml), dried ($MgSO_4$), concentrated in vacuo, and bulb-to-bulb distilled (100° C./0.2 torr) to give 2.6 g (51.5% yield) of 5-cyclopentylhexanal.

IR: 2950, 2867, 2715, 1727, 1452, 1410, 1377. $^1$H-NMR: 0.90 (d, J=6.4, 3H), 1.01–1.91 (m, 14H), 2.35–2.46 (m, 2H), 9.77 (t, J=1.8, 1H). MS: 168 (19, M$^+$), 150 (1), 135 (27), 121 (19), 109 (29), 97 (57), 96 (100), 95 (34), 81 (65), 69 (50), 68 (43), 67 (56), 55 (98), 41 (48).

Odor: aldehydic, green, fresh, hesperidic, linear.

Example 15

5-Cyclopentylhexan-1-ol

5-Cyclopentylhexanal (4.2 g; 25 mmol) in ethanol (40 ml) was added to sodium borohydride (1.2 g; 32 mmol) suspended in the same solvent (50 ml) at 10° C. The reaction mixture was stirred at room temperature for 2 hours and then 1 N HCl (50 ml) was added dropwise at 0° C. The mixture was diluted with MTBE (150 ml), the organic layer separated, washed with brine (3×250 ml), dried ($MgSO_4$), concentrated in vacuo, and bulb-to-bulb distilled (125° C./0.2 torr) to give 3.4 g (80% yield) of 5-cyclopentylhexan-1-ol.

IR: 3326, 2949, 2865, 1452, 1376, 1059. $^1$H-NMR: 0.86 (d, J=6.4, 3H), 1.01–1.82 (m, 17H), 3.63 (t, J=6.5, 2H). MS: 152 (0.7, M+—$H_2O$), 137 (3), 123 (4), 110 (14), 109 (18), 101 (14), 97 (72), 96 (49), 95 (28), 83 (80), 82 (53), 69 (33), 68 (33), 67 (47), 55 (100), 41 (35).

Odor: floral, sweet, fruity, raspberry, powdery, rosy.

Example 16

5-(2-Methylcyclopent-1-enyl)pentan-1-ol and 5-(5-methyl-cyclopent-1-enyl)pentan-1-ol 1,4-Dibromopentane (76 g; 0.33 mol) dissolved in THF (450 ml) was added at reflux within 70 minutes to magnesium turnings (15.8 g; 0.66 mol) in THF (50 ml). The mixture was refluxed for 90 minutes, cooled to room temperature and diluted with THF (250 ml). This solution was added within 160 minutes to caprolactone (37.6 g; 0.33 mol) dissolved in THF (400 ml) with the temperature maintained at 5° C. After further stirring for 90 minutes without cooling, the mixture was poured into ice-water (1.2 l), acidified to pH 2 (HCl) and extracted with MTBE (2×600 ml). The organic phases were washed with water (4×800 ml), dried ($Na_2SO_4$), concentrated in vacuo, and distilled (0.02 torr) over KHSO4 (1.3 g) to give 23 g of an oil which was further purified by flash-chromatography (MTBE/hexane 1:5) to give 4.8 g (9% yield) of a mixture of the two isomers.

IR: 3334, 2930, 2856, 1456, 1379, 1072, 1052. $^1$H-NMR: 0.99 (d, J=8, ca. 0,85H), 1.23–1.50 (m, ca. 5H), 1.52–1.69 (m, ca. 5H), 1.72–1.79 (m, 1H), 1.91–2.32 (m, 5H, 3.58–3.66(m, 2H), 5.29 (bs, ca 0.3H). MS: 168(18, M$^+$), 81 (1), 95 (2), 67 (3), 55 (4), 41 (5), 107 (6), 135 (7), 121 (8).

Odor: floral, rosy, fruity (melon), marine.

Example 17

4-(Cyclopent-1-enyl)butan-1-ol and 4-cyclopentylidene-butan-1-ol 1,4-Dibromobutane (64.8 g; 0.3 mol) dissolved in THF (300 ml) was added within 45 minutes to magnesium (14.6 g; 0.6 mol) in the same solvent (35 ml). After 3 hours with stirring at reflux, the solution was cooled to room temperature, diluted with THF (30 ml) and added within 30 minutes to β-valerolactone (30 g; 0.3 mol) dissolved in THF (450 ml) with the temperature maintained at 10° C. After stirring at room temperature for 2 hours, the reaction mixture was poured into ice-water (500 ml), acidified to pH 2 (10% HCl), and extracted with MTBE (3×200 ml). The organic phases were washed with water (3×500 ml) dried ($Na_2SO_4$), concentrated in vacuo and distilled (0.1 torr) over $KHSO_4$ (0.5 g) to afford 10.5 g of an oil which after flash-chromatography (MTBE/hexane 1:5) gave 3.4 g (8% yield) of the two isomers.

IR: 3334, 2934, 2844, 1652, 1436, 1056, 1032. $^1$H-NMR: 1.46–1.69 (m, ca. 4.5H), 1.8–1.89 (m, ca. 1.5H), 2.0–2.12 (m, 2H), 2.14–2.32 (m, 4H), 2.78 (bm, 1H), 3.61 (t, J=7, 2H), 5.24 (m, ca. 0.25H), 5.33 (t, J=1, ca. 0,75H); MS: 140 (19, M$^+$), 79(1), 67 (2), 93 (3), 41 (4), 53 (5), 31 (6), 107 (7), 122 (8).

Odor: rosy, aldehydic, green.

Example 18

6-Cyclopentyl-3-methylhexan-3-ol a) 1-Ethenylcyclopentanol

A solution of vinylbromide (146.6 g; 1.37 mol) in 250 ml of THF was added during 4 hours to a mixture of magnesium fine turnings (33.3 g; 1.37 mol) and a crystal of iodine in 150 ml of THF at t <50° C. The resulting dark grey mixture was stirred for 1 hour, treated with a solution of cyclopentanone (104.8 g; 1.25 mol) in 100 ml of THF at 35° C. to 45° C., and stirred overnight at room temperature. Saturated $NH_4Cl$ solution (1l) was added at about 0° C. and the reaction mixture was acidified to pH about 6–7 with 2N HCl. The organic layer was separated, washed with brine (3×100 ml), dried over $MgSO_4$ and concentrated in vacuo. Distillation using a Widmer column (32° C./0.06 torr) yielded 67.6 g (48% yield) of 1-ethenylcyclopentanol.

b) 5-Cyclopentylidenepentan-2-one

A 600 ml autoclave containing a mixture of 1-ethenyl-cyclopentanol (172.0 g; 1.54 mol), isopropenyl methyl ether (218.8 g; 3.04 mol), triethylamine (1.65 ml) and 85% $H_3PO_4$ (0.72 ml) was pressurized with $N_2$ at 2 bar and heated up to 125° C. An increase of the pressure to 7 bar was observed. After 14 hours stirring, the autoclave was cooled down to room temperature and depressurized. MTBE (1.5 l) was added to the mixture, washed with $H_2O$ (4×25 ml) until neutral pH, dried ($MgSO_4$) and concentrated. Distillation (61° C./0.1 torr) yielded 161.3 g (69% yield) of 5-cyclopentylidenepentan-2-one.

c) 6-Cyclopentylidene-3-methylhex-1-yn-3-ol

Acetylene was bubbled for 50 minutes through a solution of tBuOK (33.8 g; 0.30 mol) in TBF (240 ml) at 0° C. The resulting beige suspension was treated with 5-cyclopentylidenepentan-2-one (41.7 g; 0.27 mol) added dropwise for 15 minutes at 0° C. The resulting mixture was warmed gently to room temperature and quenched with saturated $NH_4Cl$ (180 ml). The aqueous phase was separated and extracted with MTBE (2×120 ml). The combined organic layers were washed with $H_2O$ (240 ml), brine (100 ml), dried over $MgSO_4$, and concentrated in vacuo. Distillation (69° C.–71° C./0.09 torr) afforded 38.95 g (81% yield) of 6-cyclopentylidene-3-methylhex-1-yn-3-ol.

d) 6-Cyclopentyl-3-methylhexan-3-ol

Hydrogenation of 6-cyclopentylidene-3-methylhex-1-yn-3-ol (5.0 g, 28 mmol) under standard conditions: $H_2$ 1 atmosphere, room temperature, over 5% Pd/C (0.57 g) in EtOH (30 ml) afforded after distillation (56° C./0.06 torr) 4.57 g (89% yield) of 6-cyclopentyl-3-methylhexan-3-ol.

IR (neat): 3378, 2942, 2866. $^1$H NMR: 0.89 (t, J=7.5 Hz, 3H), 1.00–1.13 (m, 2H), 1.14 (s, 3H), 1.48 (q; J=7.5 Hz, 2H), 1.24–1.65 (m, 11H), 1.69–1.84 (m, 3H). MS: 169 (2, M$^+$—$CH_3$), 155 (6), 137 (8), 95 (32), 81 (23), 73 (100), 67 (14), 55 (32), 43 (18), 41 (18).

Odor: floral (rosewood), fruity (apricot), hesperidic, neroli.

Example 19

5-(Cyclopent-1-enyl)-2-methylpentan-2-ol a) 5-(Cyclonent-1-enyl)-2-pentanone

A mixture of 5-cyclopentylidene-2-pentanone (9.92 g; 65 mmol) and p-TsOH (100 mg; 0.53 mmol) in toluene (150 ml) was heated at 90° C. for 8 hours, then cooled down to room temperature, diluted with MTBE (100 ml), washed with saturated $NaHCO_3$ (50 ml), $H_2O$ (50 ml), brine (50 ml), dried over $MgSO_4$ and concentrated in vacuo. Distillation under reduced pressure (48° C./0.065 torr) yielded 7.13 g of 5-(cyclopent-1-enyl)-2-pentanone (purity about 80%), which was further purified by flash chromatography to give 6.1 g (61% yield) of a 89% pure product containing 11% of 5-cyclopentylidene-2-pentanone.

b) 5-(Cyclolpent-1-enyl)-2-methylpentan-2-ol 5-(Cyclopent-1-enyl)-2-pentanone (5.95 g; 39 mmol) in ethyl ether (6 ml) was added dropwise to a 3M solution of methylmagnesium bromide in the same solvent (17 ml; 51 mmol) during 15 minutes. After 2 hours at reflux, the mixture was cooled down to room temperature, poured into ice (20 g), acidified with 5N HCl (20 ml) and extracted with MTBE (60 ml). The aqueous phase was separated and extracted again with MTBE (2×100 ml). The combined organic phases were washed with saturated $NaHCO_3$ (80 ml), $H_2O$ (80 ml), brine (80 ml), dried over $MgSO_4$ and concentrated in vacuo. Bulb-to-bulb distillation (80° C./0.06 torr) yielded quantitatively 5.84 g of 5-(cyclopent-1-enyl)-2-methylpentan-2-ol containing 11% of 5-cyclopentylidene-2-methylpentan-2-ol.

IR: 3364, 2967, 2939, 2867, 2844, 1468, 1377, 1296, 1195, 1149, 1047, 910, 772. $^1$H NMR: 1.21 (s, 6H), 1.41–1.56 (m, 4H), 1.80–1.90 (m, 2H), 2.02–2.11 (m, 2H), 2.18–2.26 (m, 2H), 2.26–2.33 (m, 2H), 5.31–5.35 (m, 1H). MS: 168 (0.5, M$^+$), 150 (28), 135 (50), 95 (25), 94 (100), 93 (16), 81 (12), 80 (14), 79 (91), 69 (22), 67 (22), 59 (34), 43 (10), 41 (12).

Odor: floral (rosy, geranium), fruity (plum), agrestic.

Example 20

5-Cyclopentylpentan-2-ol a) 5-Cyclopenlpentan-2-one

Hydrogenation of 5-cyclopentylidenepentan-2-one synthesized in example 18b (30.4 g; 0.2 mol) under standard conditions (cf. example 19d) gave, after distillation (61° C.) −67° C./0.1 torr), 25.8 g (84% yield) of 5-cyclopentylpentan-2-one.

b) 5-Cyclopentylpentan-2-ol $NaBH_4$ (3.15 g; 83 mmol) was added portionwise to a solution of 5-cyclopentylpentan-2-one (16.0 g; 104 mmol) in MeOH (125 ml) at 0° C. The mixture was stirred at 0° C. for 1 hour then at room temperature for 2 hours. Water (100 ml) was added cautiously and the mixture extracted with MTBE (3×250 ml). The organic phases were combined, washed with brine (3×50 ml), dried over $MgSO_4$, concentrated in vacuo and distilled (52° C.–56° C./0.045 torr) to give 14.5 g (90% yield) of 5-cyclopentylpentan-2-ol.

IR: 3347, 2947, 2861, 1453, 1374, 1308, 1116, 1077, 942. $^1$H NMR: 1.00–1.12 (m, 2H), 1.18 (d, J=6.0, 3H), 1.23–1.38 (m, 3H), 1.38–1.64 (m, 7H), 1.67 (bs, 1H), 1.70–1.80 (m, 3H), 3.73–3.85 (m, 1H). MS: 141 (6, M$^+$—$CH_3$), 123 (18), 111 (16), 110 (22), 96 (52), 95 (48), 83 (28), 82 (70), 81 (60), 69 (42), 68 (36), 67 (84), 58 (12), 55 (34), 45 (100), 43 (16), 41 (35), 39 (12).

Odor: floral (tuberose), lily of the valley, coconut, celery.

Example 21

5-Cyclopentylidene-2-methylpentan-2-ol

5-Cyclopentylidene-2-pentanone (13.4 g; 88 mmol) in ether (13 ml) was added dropwise during 30 minutes to a 3M solution of methylmagnesium bromide in ether (38 ml; 114 mmol). After addition of more ether (25 ml), the mixture was heated under reflux for 2 hours, then cooled down to room temperature, poured into ice (40 g), acidified with 5N HCl (50 ml) and extracted with MTBE (130 ml). The aqueous phase was separated and extracted with MTBE (2×130 ml). The combined organic phases were washed with saturated $NaHCO_3$ (2×130 ml), water (130 ml), dried over $MgSO_4$ and concentrated in vacuo. Distillation (52° C.–55° C./0.06 torr) yielded 11.24 g (76% yield) of 5-cyclopentylidene-2-methylpentan-2-ol.

IR: 3366, 2959, 2867, 1451, 1377, 1218, 1147, 910. $^1H$ NMR: 1.21 (s, 6H), 1.48–1.70 (m, 6H), 2.00–2.09 (m, 2H), 2.15–2.24 (m, 4H), 5.20–5.28 (m, 1H). MS: 168 (0.5, $M^+$), 150 (65), 135 (100), 121 (12), 107 (26), 95 (46), 94 (68), 93 (32), 82 (30), 81 (13), 80 (10), 79 (63), 67 (40), 59 (42), 55 (10), 43 (12), 41 (16).

Odor: floral ionone, linalool, raspberry, agrestic, tea.

Example 22

5-Cyclouentylidenepent-2-yl propanoate a) 5-CYclopentylidenegentan-2-ol 5-cyclopentylidenepentan-2-one (22.7 g; 149 mmol) was reduced, as in example 20b, to give 24.5 g of crude 5-cyclopentylidenepentan-2-ol that was used without further purification in the following step.

b) 5-Cyclopentylidenepent-2-yl propanoate

DMAP (0.03 g; 0.24 mnol) was added to a mixture of 5-cyclopentylidenepentan-2-ol (5.0 g; 32 mmol), propionic anhydride (6.7 ml, 52 mmol), and $Et_3N$ (7.2 ml, 52 mmol). After 1.5 hours stirring at room temperature, the reaction mixture was diluted with MTBE (140 ml), washed with 2N HCl (60 ml), water (60 ml), saturated $NaHCO_3$ (60 ml), again with water (60 ml), and brine (60 ml), dried over $MgSO_4$ and concentrated in vacuo. Distillation under reduced pressure (87° C.–92° C./0.04 torr) afforded 5.38 g (80% yield) of 5-cyclopentylidenepent-2-yl propanoate.

IR:2943,2868, 1736,1462,1370,1192, 1129,1082. $^1HNMR$: 1.14(t,J=7.6,3H), 1.21 (d, J=6.0, 3H), 1.46–1.70 (m, 6H), 1.91–2.07 (m, 2H), 2.10–2.18 (m, 2H), 2.18–2.25 (m, 2H), 2.30 (q, J=7.6, 2H), 4.85–4.95 (m, 1H), 5.17–5.25 (m, 1H). MS: 195 (0.5, $M^+$—$CH_3$), 136 (100), 121 (57), 107 (60), 95 (54), 94 (72), 93 (66), 91 (14), 81 (18), 80 (28), 79 (73), 77 (11), 68 (31), 67 (35), 57 (34), 41 (15).

Odor: floral, fruity, pear, ionone, apple.

Example 23

EXAMPLE 23

| Shower gel perfume | |
|---|---|
| 5-Cyclopentylhexanenitrile 10% DPG | 7.5 |
| Aldehyde C 12 lauric 10% DPG | 10 |
| Ambrettolide | 10 |
| Benzyl acetate | 30 |
| Bergamote abergapt oil | 115 |
| Berryflor | 3 |
| Cetone alpha | 40 |
| Citronellol E | 20 |
| Citronellyl acetate | 10 |
| Coumarin pure crist. | 20 |
| Dipropylene glycol | 117 |
| Ethyl linalool | 35 |
| Ethyl vanillin | 5 |
| Ethylene brassylate | 130 |
| Eucalyptol | 4 |
| Eugenol pur | 5 |
| Givescone | 3 |
| Hexyl cinnamic aldehyde | 200 |
| Ionone beta | 10 |
| Lemonile | 3 |
| Lilial | 30 |
| Myraldene | 3 |
| Orange Floride oil | 30 |
| Prunolide | 10 |
| Radjanol | 40 |
| Rhodinol 70 | 10 |
| Tricyclal | 3 |
| Tuberose base (reconstitution) | 7.5 |
| Verdantiol | 4 |
| Vertofix coeur | 50 |
| Ylang ylang oil | 35 |
| | 1000 |

5-Cyclopentylhexanenitrile brings a lot of diffusion to the fragrance, imparting a very rich orris, ionone effect to the composition; the floral rosy/lily of the valley part of the fragrance is also considerably enhanced; this compound brings both power and elegance to this shower gel perfume.

Example 24

EXAMPLE 24

| Fine fragrance for men | |
|---|---|
| 5-Cyclopentylhexan-1-ol 10% DPG | 30 |
| Amyris oil | 50 |
| Benzoin tears Siam 50% DBP | 50 |
| Bergamote Italy oil | 175 |
| Cepionate | 60 |
| Citronellyl acetate | 25 |
| Damascenone 10% DPG | 10 |
| Dihydrolinalool | 50 |
| Dimethylbenzylcarbinol isobutyrate | 6 |
| Dimetol | 40 |
| Fennaldehyde | 15 |
| Fixambrene | 4 |
| Florhydral | 5 |
| Florol | 50 |
| Gardenol | 5 |
| Laurine | 80 |
| Lemon Italy oil | 40 |
| Magnolione | 80 |
| Mandarin green Italy oil | 10 |
| Olibanum res. 50% DBP | 45 |
| Orange Florida oil | 60 |
| Thibetolide | 10 |
| Tricyclal 10% DPG | 25 |
| Tropional | 40 |
| Undecavertol | 15 |
| Velvione | 20 |
| | 1000 |

5-Cyclopentylhexan-1-ol brings on the whole higher diffusion to the blend. It enhances hesperidic notes, particularly mandarin effect. The aldehydic rosy effect it imparts adds to the transparency of the fragrance and to its modernity through marine undertones.

Example 25

EXAMPLE 25

| Deodorant fragrance | |
|---|---|
| 5-Cyclopentylhexanal 10% DPG | 30 |
| Bergamote base | 50 |
| Cedryl acetate | 25 |
| Cepionate | 50 |
| Coumarin | 5 |
| Cyclohexyl salicylate | 12 |
| Dipropylene glycol | 105 |
| Dynascone 10 | 15 |
| Elemi oil | 5 |
| Fixambrene | 5 |
| Folrosia | 6 |
| Hydro Rose C (rose oil reconstitution) | 300 |
| Iso E Super | 85 |
| Juniper berries oil | 20 |
| Kephalis | 30 |
| Lemon Italy oil | 50 |
| Mate absolute 10% DPG | 35 |
| Metambrate | 45 |
| Methyl Pamplemousse | 8 |
| Nutmeg oil | 8 |
| Okoumal | 10 |
| Patchouli SF oil | 8 |
| Sandalore | 35 |
| Spearmint USA 10% DPG | 20 |
| Thibetolide | 30 |
| | 1000 |

5-Cyclopentylhexanal brings higher harmony to the blend. It imparts anisic, tarragon type of nuances, along with its natural rosy/geranium effect. Through evaporation, the anisic undertones evolve toward a floral, marine, anisic cocktail which underlines the modern transparent and clean effect of the fragrance in the deodorant application.

For the exact definition of the trivial names set forth above, see Flavor and *Fragrance Materials* 1998, Allured Publishing Corporation, Carol Stream, Ill., U.S.A. or Arctander, Perfume and Flavor Chemicals—1969, which is incorporated by reference as if recited in full herein.

The invention being thus described, it will be obvious that the same may be varied in many ways. Such variations are not to be regarded as a departure from the spirit and scope of the invention and all such modifications are intended to be included within the scope of the following claims.

What is claimed is:

1. A compound of formula II

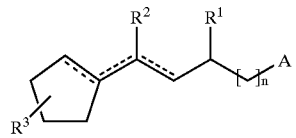

wherein

A is selected from the group consisting of $CR^4R^5OH$ and $C(O)R_4$;

$R^1$, $R^3$, $R^4$ and $R^5$ are independently H or $C_{1-3}$-alkyl;

$R^2$ is H, $C_{1-3}$-alkyl, methylene or ethylidene;

n is 0 or 1; and,

=== is a single or double bond, wherein a maximum of 2 double bonds are present in the compound.

2. A composition comprising a compound according to claim 1 in combination with an odorant composition.

3. A method for imparting a fragrance to a substrate comprising applying to the substrate a compound according to claim 1.

* * * * *